United States Patent [19]

Blanchard et al.

[11] 4,054,583

[45] Oct. 18, 1977

[54] PROCESS FOR CONVERTING 2,7-DIHYDROXY-5-ISOPROPYLIDENE-9-SUBSTITUTED-2,6-METHANO-3,4,5,6-TETRAHYDRO-2H-1-BENZOXOCIN TO TRANS-1-HYDROXY-3-SUBSTITUTED-6,6-DIMETHYL-6,6A,7,8,10,10A-HEXAHYDRO-9H-DIBENZO(B,D)PYRAN-9-ONE

[75] Inventors: William B. Blanchard; Charles W. Ryan, both of Indianapolis, Ind.

[73] Assignee: Eli Lilly and Company, Indianapolis, Ind.

[21] Appl. No.: 702,808

[22] Filed: July 6, 1976

[51] Int. Cl.$^2$ .................................. C07D 311/78
[52] U.S. Cl. .................... 260/345.3; 260/345.2
[58] Field of Search .............. 260/345.3, 702, 804–809

[56] References Cited

U.S. PATENT DOCUMENTS

| 2,419,936 | 5/1947 | Adams | 260/345.3 |
| 3,560,528 | 2/1971 | Petrzilka | 260/345.3 |
| 3,700,661 | 10/1972 | Saucy | 260/345.3 |
| 3,816,458 | 6/1974 | Saucy | 260/345.3 |

OTHER PUBLICATIONS

Razdan et al., J. Am. Chem. Soc., 96, 5860 (1974).
Razdan et al. (I), Tet. Letters, pp. 4947–50 (1969).

*Primary Examiner*—James O. Thomas, Jr.
*Assistant Examiner*—Nicky Chan
*Attorney, Agent, or Firm*—Charles W. Ashbrook; Everet F. Smith

[57] ABSTRACT

Reaction of an aluminum halide with a 2,7-dihydroxy-5-isopropylidene-9-substituted-2,6-methano-3,4,5,6-tetrahydro-2H-1-benzoxocin in an organic solvent effects cleavage of the pyran ring system with concomitant recyclization to provide exclusively a trans-1-hydroxy-3-substituted-6,6-dimethyl-6,6a,7,8,10,10a-hexahydro-9H-dibenzo[b,d]pyran-9-one.

7 Claims, No Drawings

PROCESS FOR CONVERTING 2,7-DIHYDROXY-5-ISOPROPYLIDENE-9-SUBSTITUTED-2,6-METHANO-3,4,5,6-TETRAHYDRO-2H-1-BENZOXOCIN TO TRANS-1-HYDROXY-3-SUBSTITUTED-6,6-DIMETHYL-6,6A,7,8,10,10A-HEXAHYDRO-9H-DIBENZO(B,D)PYRAN-9-ONE

BACKGROUND OF THE INVENTION

Certain hexahydro-dibenzo [b,d] pyran-9-ones are known to be useful drugs. As described in U.S. Pat. Nos. 3,928,598, 3,944,673, and 3,953,603, dl-trans-1-hydroxy-3-(1,1-dimethylheptyl)-6,6-dimethyl-6,6a,7,8,10,10a-hexahydro-9H-dibenzo[b,d]pyran-9-one is of particular importance in the treatment of anxiety and depression. The preparation of such compounds suffer from being multistep and of low yields. Fahrenholtz, Lurie and Kierstead, J. Am. Chem. Soc. 88, 2079 (1966), 89, 5934 (1967), describe the synthesis of such hexahydro-dibenzo[b,d]pyranones by reaction of a 5-alkyl resorcinol with diethyl α-acetylglutarate to form an ethyl 4-methyl-5-hydroxy-7-alkylcoumarin-3-propionate, which compound is cyclized by reaction with a metal hydride to afford a 1-hydroxy-3-alkyl-7,10-dihydro-6H-dibenzo[b,d]-pyran-6,9 (8H)-dione. The latter compound is ketalized at the 9-position, and then reacted with methyl magnesium bromide to provide, after de-ketalization, a 1-hydroxy-3-alkyl-6,6-dimethyl-6a,7,8,9-tetrahydro-6H-dibenzo[b,d]-pyran-one, which upon reduction by lithium in ammonia provides predominantly the corresponding dl-trans-1-hydroxy-3-alkyl-6,6-dimethyl-6,6a,7,8,10,10a-hexahydro-9H-dibenzo[b,d]pyran-9-one, with minor quantities of the less active 6a,10a-cis isomer.

This invention relates to a one-step process for preparing substantially exclusively trans-1-hydroxy-3-substituted-6,6-dimethyl-6,6a,7,8,10,10a-hexahydro-9H-dibenzo[b,d]pyran-9-ones from 2,6-methano-2H-1-benzoxocin derivatives. While certain 2,6-methano-2H-1-benzoxocin derivatives are known, none have been used as intermediates in the preparation of dibenzopyranone compounds. Razdan et al., J. Am. Chem. Soc., 96 5860 (1974), reported the synthesis of 2-methyl-5-isopropylidene-7-hydroxy-9-pentyl-2,6-methano-3,4,5,6-tetrahydro-2H-1-benzoxocin from the reaction between 5-pentyl resorcinol and 1-methyl-1-hydroxy-4-(2-propenyl)-2-cyclohexene. Such benzoxocin was reported not to be convertible to a dibenzopyran derivative. Additionally, Razdan and Zitko reported the conversion of 1-hydroxy-3-n-pentyl-6,6,9-trimethyl-6aα,7,8,10aβ-tetrahydro-6H-dibenzo[b,d]pyran to 2-methyl-5-isopropylidene-7-hydroxy-9-pentyl-2,6-methano-2H-1-benzoxocin, Tetrahedron Letters, 4947 (1969). These workers reported that the benzoxocin derivative is in equilibrium with the dibenzopyran derivative, but that such equilibrium heavily favors the benzoxocin. The efficient conversion of a 2,6-methano-2H-1-benzoxocin to a dibenzopyranone derivative has not heretofore been reported. An object of this invention is to provide a process for converting a 2H-1-benzoxocin to substantially exclusively a 6a,10a-trans-hexahydrodibenzopyranone.

SUMMARY OF THE INVENTION

This invention provides a process for preparing a compound of the formula

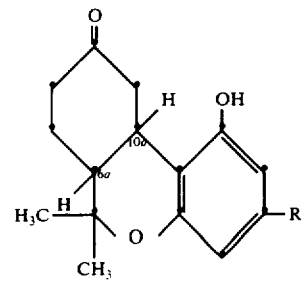

wherein R is $C_5-C_{10}$ alkyl, $C_5-C_{10}$ alkenyl, $C_5-C_8$ cycloalkyl, or $C_5-C_8$ cycloalkenyl, and wherein the hydrogen atoms attached at the 6a and 10a positions are oriented trans to one another; which process comprises reacting from about 2 to about 6 molar equivalents of an aluminum halide selected from aluminum chloride and aluminum bromide with a 2,7-dihydroxy-5-isopropylidene-9-substituted-2,6-methano-3,4,5,6-tetrahydro-2H-1-benzoxocin having the general structural formula

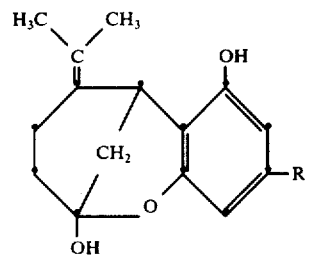

in which R has the above-defined meaning. The process is carried out in an halogenated hydrocarbon or aromatic solvent and at a temperature ranging from about −20° C. to about 100° C. The preferred reaction solvent is a halogenated hydrocarbon, especially dichloromethane, and the preferred reaction temperature is within the range of about 0° C. to about 80° C.

DETAILED DESCRIPTION OF THE INVENTION

In the above formulas, R represents $C_5-C_{10}$ alkyl, $C_5-C_{10}$ alkenyl, $C_5-C_8$ cycloalkyl, and $C_5-C_8$ cycloalkenyl. The term "$C_5-C_{10}$ alkyl" refers to both straight and branched chain alkyl groups, examples of which include n-pentyl, n-octyl, 1-methylnonyl, 1,2-dimethylheptyl, 1,2,3-trimethylhexyl, 1-ethyl-2-methylbutyl, isohexyl, and related groups. Examples of $C_5-C_{10}$ alkenyl groups include 2-pentenyl, 3-hexenyl, 5-decenyl, 1,1-dimethyl-2-heptenyl, 1,2-dimethyl-1-heptenyl, 1,2-diethyl-2-butenyl, 1,2,2,3-tetramethyl-3-hexenyl, and 1-methyl-1-heptenyl. Typical $C_5-C_8$ cycloalkyl groups include cyclopentyl, cyclohexyl, and cyclooctyl, and examples of $C_5-C_8$ cycloalkenyl include 1-cyclopentenyl, 1-cyclohexenyl, 2-cycloheptenyl, and 3-cyclooctenyl.

In accordance with the process of this invention, a 2,7-dihydroxy-5-isopropylidene-9-substituted-2,6-methano-2H-1-benzoxocin is reacted with an aluminum halide selected from aluminum chloride and aluminum bromide, preferably aluminum chloride. The quantity of aluminum halide routinely incorporated in the process ranges from about a 2 molar excess to about a 6 molar excess; however, larger quantities can be utilized if desired. The process is carried out in an halogenated hydrocarbon or aromatic solvent such as dichloromethylane, dibromomethane, 1,2-dichloroethane, 1,1-dibromoethane, chloropropane, chlorobenzene, bromobenzene, benzene, toluene, xylene, and the like. The preferred reaction solvent is dichloromethane. The process proceeds efficiently at a temperature within the range of about −20° C. to about 100° C., and is preferably carried out at a temperature from about 0° C. to about 80° C. The conversion of the benzoxocin derivative to the corresponding 6a,10a-trans-hexahydrodibenzo[b,d]pyran-9-one derivative is substantially complete within about 0.5 to about 8 hours; however, longer reaction times are not detrimental and can be utilized if desired. The dibenzo[b,d]pyranone product of the above conversion is readily isolated by simply washing the reaction mixture with water, or if desired by washing with a dilute mineral acid such as hydrochloric acid, and then evaporating the organic reaction solvent. The residual product thus isolated can be further purified if desired by any conventional technique, such as chromatography or crystallization from solvents such as hexane and cyclohexane.

The 2,7-dihydroxy-5-isopropylidene-9-substituted-2,6-methano-3,4,5,6-tetrahydro-2H-1-benzoxocin which is a required starting material for the process of this invention is conveniently prepared by reacting the appropriate 5-substituted resorcinol with 1-methoxy-4-(1-hydroxy-1-methylethyl)-1,4-cyclohexadiene in the presence of a suitable catalyst such as boron tribromide, boron trifluoride, or zinc chloride. When the reaction is carried out in the presence of about an equimolar quantity of a catalyst such as boron trifluoride, the product is a 2-methoxy-5-isopropylidene-7-hydroxy-9-substituted-2,6-methano-2H-1-benzoxocin. Alternatively, the 5-substituted resorcinol can be reacted with 1-methoxy-4-(1-hydroxy-1-methylethyl)-1,4-cyclohexadiene in the presence of an excess of a catalyst such as boron trifluoride or zinc chloride, for instance a 0.5 to 2 molar excess, thereby affording directly the corresponding 2,7-dihydroxy-5-isopropylidene-9-substituted-2,6-methano-3,4,5,6-tetrahydro-2H-1-benzoxocin. It should be noted that aluminum halides fail to effect condensation of a resorcinol with 1-methoxy-4-(1-hydroxy-1-methylethyl)-1,4-cyclohexadiene.

Examples of 2.7-dihydroxy-5-isopropylidene-9-substituted-2,6-methano-3,4,5,6-tetrahydro-2H-1-benzoxocins routinely reacted with an aluminum halide according to the process of this invention to provide the corresponding trans-1-hydroxy-3-substituted-6,6-dimethyl-6,6a,7,8,10,10a-hexahydro-9H-dibenzo[b,d]pyran-9-one include the following:
  2,7-dihydroxy-5-isopropylidene-9-(1,1-dimethylheptyl)-2,6-methano-3,4,5,6-tetrahydro-2H-1-benzoxocin;
  2,7-dihydroxy-5-isopropylidene-9-n-pentyl-2,6-methano-3,4,5,6-tetrahydro-2H-1-benzoxocin;
  2,7-dihydroxy-5-isopropylidene-9-(1,2-dimethyl-1-heptenyl)-2,6-methano-3,4,5,6-tetrahydro-2H-1-benzoxocin;
  2,7-dihydroxy-5-isopropylidene-9-(3-octenyl)-2,6-methano-3,4,5,6-tetrahydro-2H-1-benzoxocin;
  2,7-dihydroxy-5-isopropylidene-9-cyclohexyl-2,6-methano-3,4,5,6-tetrahydro-2H-1-benzoxocin;
  2,7-dihydroxy-5-isopropylidene-9-(1-cyclooctenyl)-2,6-methano-3,4,5,6-tetrahydro-2H-1-benzoxocin;
and the like.

It will be noted that the process of this invention provides substantially exclusively a trans-1-hydroxy-3-substituted-6,6-dimethyl-6,6a,7,8,10,10a-hexahydro-9H-dibenzo[b,d]pyran-9-ones. Such compounds are those in which the hydrogen atoms attached at the 6a and the 10a-positions are oriented trans to one another, and the process can provide a dl- mixture of such trans isomers. In particular, the process of this invention provides compounds having a 6a$\beta$-hydrogen atom and a 10a$\alpha$-hydrogen atom, in addition to those compounds having a 6a$\alpha$-hydrogen atom and a 10a$\beta$-hydrogen atom. The dl-trans-1-hydroxy-3-substituted-6,6-dimethyl-6,6a,7,8,10,10a-hexahydro-9H-dibenzo[b,d]pyran-9-ones prepared according to this invention are useful as psychotropic drugs as well as intermediates in the preparation of other useful drugs, for instance as described in U.S. Pat. Nos. 3,507,885 and 3,636,058. Certain of the compounds prepared according to the process of this invention recently have been found to be especially useful as anti-anxiety and anti-depressant drugs. Of particular importance is dl-trans-1-hydroxy-3-(1,1-dimethylheptyl)-6,6-dimethyl-6,6a,7,8,10,10a-hexahydro-9H-dibenzo[b,d]pyran-9-one, as described for example in U.S. Pat. No. 3,928,598.

It should be noted that the process of this invention provides substantially exclusively a trans-hexahydrodibenzo[b,d]pyran-9-one derivative. The process is therefore of utmost importance since it is preferred not to prepare a dl-cis-dibenzo[b,d]pyran-9-one, as these latter compounds are only minimally active pharmacologically.

In an effort to more fully describe the process of the invention, the following detailed examples are provided by way of exemplification.

EXAMPLE 1

2,7-dihydroxy-5-isopropylidene-9-(1,1-dimethylheptyl)-2,6-methano-3,4,5,6-tetrahydro-2H-1-benzoxocin.

A solution of 1.0 g. of 1-methoxy-4-(1-hydroxy-1-methylethyl)-1,4-cyclohexadiene and 1.18 g. of 5-(1,1-dimethylheptyl)resorcinol in 40 ml. of dichloromethane was cooled to 5° C. in an ice-water bath and stirred while 1.5 ml. of boron trifluoride diethyl etherate was added to the mixture in one portion. The reaction mixture then was stirred at 5° C. for 5 hours. The reaction mixture then was washed with aqueous sodium bicarbonate solution and dried. The solvent was removed by evaporation under reduced pressure to provide the product as an oil. The oil so formed was triturated with n-hexane and then allowed to stand at room temperature for 12 hours, during which time the oil solidified. The solid product was collected by filtration and was recrystallized from 10 ml. of methyl cyclohexane to afford 580 mg. of 2,7-dihydroxy-5-isopropylidene-9-(1,1-dimethylheptyl)-2,6-methano-3,4,5,6-tetrahydro-2H-1-benzoxocin. M.P. 158°–159° C.

Analysis Calc. for $C_{24}H_{36}O_3$
Theory: C, 77.38; H, 9.74.
Found: C, 77.33; H, 9.55.

EXAMPLE 2 dl-trans-1-hydroxy-3-(1,1-dimethylheptyl)-6,6-dimethyl-6,6a,7,8,10,10a-hexahydro-9H-dibenzo[b,d]pyran-9-one A solution of 100 mg. of 2,7-dihydroxy-5-isopropylidene-9-(1,1-dimethylheptyl)-2,6-methano-3,4,5,6-tetrahydro-2H-1-benzoxocin in 5 ml. of dichloromethane was stirred at 24° C. while 100 mg. of aluminum chloride was added to the solution in one portion. The reaction mixture was stirred for 6 hours at 24° C., and then was washed with 1N hydrochloric acid solution and with water. After drying the reaction mixture, the solvent was removed by evaporation under reduced pressure, providing dl-trans-1-hydroxy-3-(1,1-dimethylheptyl)-6,6-dimethyl-6,6a,7,8,10,10a-hexahydro-9H-dibenzo[b,d]pyran-9-one. M.P. 160°-161° C.

nmr (CDCl₃): 67 Hz (s, 3H, C-6 methyl)

88 Hz (s, 3H, C-6 methyl)

We claim:

1. A process for preparing a compound of the formula

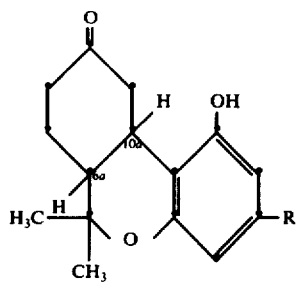

wherein:

R is $C_5-C_{10}$ alkyl, $C_5-C_{10}$ alkenyl, $C_5-C_8$ cycloalkyl, or $C_5-C_8$ cycloalkenyl; and wherein the hydrogen atoms attached at the 6a and 10a positions are oriented trans to one another; comprising reacting a 2,7-dihydroxy-5-isopropylidene-9-substituted-2,6-methano-3,4,5,6-tetrahydro-2H-1-benzoxocin of the formula

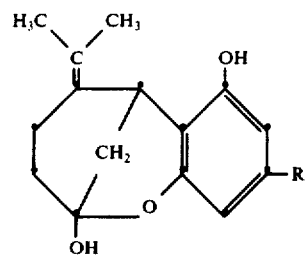

wherein R has the above-defined meaning, with from about 2 to about 6 molar equivalents of an aluminum halide selected from aluminum chloride and aluminum bromide, in a halogenated hydrocarbon or aromatic solvent, at a temperature ranging from about −20° C. to about 100° C.

2. The process according to claim 1 wherein the reaction solvent is a halogenated hydrocarbon selected from dichloromethane, dibromomethane, 1,2-dichloroethane, 1,1-dibromoethane, chloropropane, chlorobenzene, and bromobenzene.

3. The process according to claim 1 wherein the aluminum halide is aluminum chloride.

4. The process according to claim 3 wherein the reaction solvent is dichloromethane.

5. The process according to claim 1 wherein the reaction temperature ranges from about 0° C. to about 80° C.

6. The process according to claim 1 wherein the 2,7-dihydroxy-5-isopropylidene-9-substituted-2,6-methano-2H-1-benzoxocin is reacted with from about 2 to about 6 molar equivalents of aluminum chloride in dichloromethane at a temperature of about 0° C. to about 80° C.

7. The process according to claim 1 wherein 2,7-dihydroxy-5-isopropylidene-9-(1,1-dimethylheptyl)-2,6-methano-2H-1-benzoxocin is reacted with from about 2 to about 6 molar equivalents of aluminum chloride in dichloromethane at a temperature of about 0° C. to about 80° C., to provide dl-trans-1-hydroxy-3-(1,1-dimethylheptyl)-6,6-dimethyl-6,6a,7,8,10,10a-hexahydro-9H-dibenzo-[b,d]pyran-9-one.

* * * * *